United States Patent
Tornier et al.

(10) Patent No.: US 6,824,567 B2
(45) Date of Patent: ***Nov. 30, 2004

(54) METHOD OF POSITIONING A MALLEOLAR IMPLANT FOR PARTIAL OR TOTAL ANKLE PROSTHESIS

(75) Inventors: Alain Tornier, Saint Ismier (FR); Michel Bonnin, Francheville (FR); Jean-Alain Colombier, Balma (FR); Thierry Judet, Ville d'Avray (FR)

(73) Assignee: Tornier, Saint Ismier (FR)

( * ) Notice: Subject to any disclaimer, the term of this patent is extended or adjusted under 35 U.S.C. 154(b) by 79 days.

This patent is subject to a terminal disclaimer.

(21) Appl. No.: 10/254,985

(22) Filed: Sep. 26, 2002

(65) Prior Publication Data

US 2003/0023315 A1 Jan. 30, 2003

Related U.S. Application Data

(62) Division of application No. 09/631,938, filed on Aug. 3, 2000, now Pat. No. 6,488,712.

(30) Foreign Application Priority Data

Aug. 3, 1999 (FR) ............................................. 99 10340

(51) Int. Cl.[7] .................................................. A61F 2/42
(52) U.S. Cl. .................................................... 623/21.18
(58) Field of Search .......................... 623/21.18, 21.11, 623/18.11; 606/96, 232, 233, 86, 87

(56) References Cited

U.S. PATENT DOCUMENTS

| | | | | |
|---|---|---|---|---|
| 3,987,500 A | | 10/1976 | Schlein | |
| 4,069,518 A | * | 1/1978 | Groth et al. | 623/21.18 |
| 4,235,428 A | | 11/1980 | Davis | |
| 5,176,682 A | * | 1/1993 | Chow | 606/72 |
| 5,236,445 A | * | 8/1993 | Hayhurst et al. | 606/232 |
| 5,306,290 A | * | 4/1994 | Martins et al. | 606/232 |
| 5,354,298 A | * | 10/1994 | Lee et al. | 606/72 |
| 5,380,334 A | * | 1/1995 | Torrie et al. | 606/104 |
| 5,423,860 A | * | 6/1995 | Lizardi et al. | 606/232 |
| 5,464,427 A | * | 11/1995 | Curtis et al. | 606/232 |
| 5,480,403 A | * | 1/1996 | Lee et al. | 606/72 |
| 5,486,197 A | * | 1/1996 | Le et al. | 606/232 |
| 5,674,224 A | * | 10/1997 | Howell et al. | 606/88 |
| 6,086,591 A | * | 7/2000 | Bojarski | 606/64 |
| 6,488,712 B1 | * | 12/2002 | Tornier et al. | 623/21.18 |
| 6,616,694 B1 | * | 9/2003 | Hart | 623/13.14 |
| 6,685,706 B2 | * | 2/2004 | Padget et al. | 606/72 |

FOREIGN PATENT DOCUMENTS

| | | |
|---|---|---|
| EP | 0864304 | 9/1998 |
| FR | 2700462 | 7/1994 |

* cited by examiner

Primary Examiner—Alvin Stewart
(74) Attorney, Agent, or Firm—Dowell & Dowell, P.C.

(57) ABSTRACT

A method of positioning a malleolar implant for partial or total ankle prosthesis wherein the implant includes a head intended to bear against the astragalus or astragalian prosthetic component and a shank provided to be introduced in a bore in the fibula including providing an orifice in the shank and inserting the implant in the bore by use of force applied along a flexible traction member extending through the orifice.

3 Claims, 4 Drawing Sheets

METHOD OF POSITIONING A MALLEOLAR IMPLANT FOR PARTIAL OR TOTAL ANKLE PROSTHESIS

CROSS REFERENCE TO RELATED APPLICATIONS

This application is a divisional application of Ser. No. 09/631,938 filed Aug. 3, 2000 now U.S. Pat. No. 6,488,712B1 and claiming priority from French application Serial Number 99 10340 filed Aug. 5, 1999.

BACKGROUND OF THE INVENTION

1. Field of the Invention

The present invention relates to a malleolar implant for a partial or total prosthesis of the ankle and to an ancillary tool for placing such an implant.

2. Description of the Related Art

It is known, for example from EP-A-0 864 304, to fit an ankle prosthesis with a malleolar implant intended to bear against an articular surface at the level of the astragalus, whether it be question of a natural surface or of a surface of a prosthetic component. During an operation on an ankle, access to the internal articular surfaces is limited by the ligamentary system which does not necessarily allow a sufficient dislocation of the joint. In particular, access to the internal surface of the fibular malleolus may be insufficient, which induces difficulties in positioning the implant, particularly by impaction.

With reference to the embodiments of FIGS. 4 and 5, it is envisaged in EP-A-0 864 304 to introduce an implant from the outer face of the fibula. However, this necessarily limits the surface of the head of this implant, which must be less than or equal to the surface of the orifice provided in the bone, so that it is necessarily of relatively small dimensions with the result of substantially fragilizing the malleolus.

For the foregoing reasons, the positioning of the malleolar implants in the known prostheses is not entirely satisfactory.

It is a particular object of the present invention to overcome these drawbacks by proposing a novel malleolar implant which may be positioned precisely, even though access to the internal surface of the fibular malleolus may be limited and whereas its articular head presents dimensions allowing it to perform its function efficiently.

SUMMARY OF THE INVENTION

To that end, the invention relates to a malleolar implant comprising a head, intended to bear against the astragalus or an astragalian prosthetic component and a shank provided to be introduced in a bore in the fibula, characterized in that the shank is provided with means for hooking a traction member adapted to be maneuvered from the outer side of the fibula, in order to position the shank in the bore.

Thanks to the invention, the implant may be prepositioned towards the inner face of the fibular malleolus and pulled through the through bore provided in the malleolus, with the result that the surgeon does not have to manipulate the implant with precision inside the joint, i.e. between the fibula and the tibia or between the fibula and the astragalus. The surgeon may exert an efficient effort on the traction member, which may be a flexible tie such as a suture thread, without being hindered by the surrounding bones. As a result, the positioning of the shank of the implant in the bore in the fibula may be precise, in particular due to the fact that the outer diameter of the shank may be substantially equal to the inner diameter of this bore, as the effort of traction which may be exerted from the outside of the fibula may be intense.

According to an advantageous aspect of the invention, the shank is provided with at least one orifice for passage of a flexible tie adapted to be engaged through the bore. In particular, the shank may comprise a plurality of orifices for passage of a flexible tie, such orifices being distributed over the length of this shank.

According to another advantageous aspect of the invention, the shank is provided with means for axial hold inside the bore. These means, which may be formed by outer radial flanges distributed over the length of the shank, make it possible efficiently to immobilize the shank inside the bore after it has been introduced therein by traction on the flexible member or tie.

The invention also relates to an ancillary tool for placing a malleolar implant as described hereinabove and, more specifically, a tool which comprises a spacer-block adapted to be inserted between the tibia and the astragalus of an ankle, and a lug fast with this spacer block and extending up to the vicinity of the outer surface of the fibular malleolus when the spacer block is in place between the tibia and the astragalus, this lug supporting a guide for boring the malleolus from its outer surface.

Thanks to the invention, the bore of the fibular malleolus may be effected from its outer surface and in the direction of its inner surface, with a determined relative positioning with respect to the tibia and the astragalus, with the result that the position of the malleolar implant in place in this bore is determined with precision with respect to the respective articular surfaces of the astragalus or of the tibia or of corresponding prosthetic components. The spacer block may be provided to cooperate with natural articular surfaces of the tibia and/or of the astragalus or with surfaces created by resection of these bones, in the case of placing a total ankle prosthesis.

According to an advantageous aspect of the invention, the spacer block is provided with a housing for receiving a shim of thickness adapted to the distance between the lower surface of the tibia and upper surface of the astragalus. This aspect of the invention makes it possible to maintain a distance corresponding to that which will be subsequently created by the prosthetic elements mounted in the lower part of the tibia and in the upper part of the astragalus, when the position of the malleolar implant is determined.

According to another advantageous aspect of the invention, the lug is articulated on the spacer block, with a limited possibility of pivoting. This makes it possible to adjust the position of the malleolus bore guide about the pivot axis of the lug with respect to the spacer block. In that case the spacer block and the lug are advantageously provided with orifices for passage of a common pivot pin.

It is also possible for the bore guide to be associated with a device for clamping the malleolus against a bearing surface formed on the lug or the spacer block. This allows a firm immobilization of the fibular malleolus during boring and thus ensures precision of the boring operation.

BRIEF DESCRIPTION OF THE DRAWINGS

The invention will be more readily understood on reading the following description of an embodiment of a malleolar implant and its ancillary tool according to the invention, given solely by way of example and with reference to the accompanying drawings, in which.

DESCRIPTION OF PREFERRED EMBODIMENT

Figure 1:
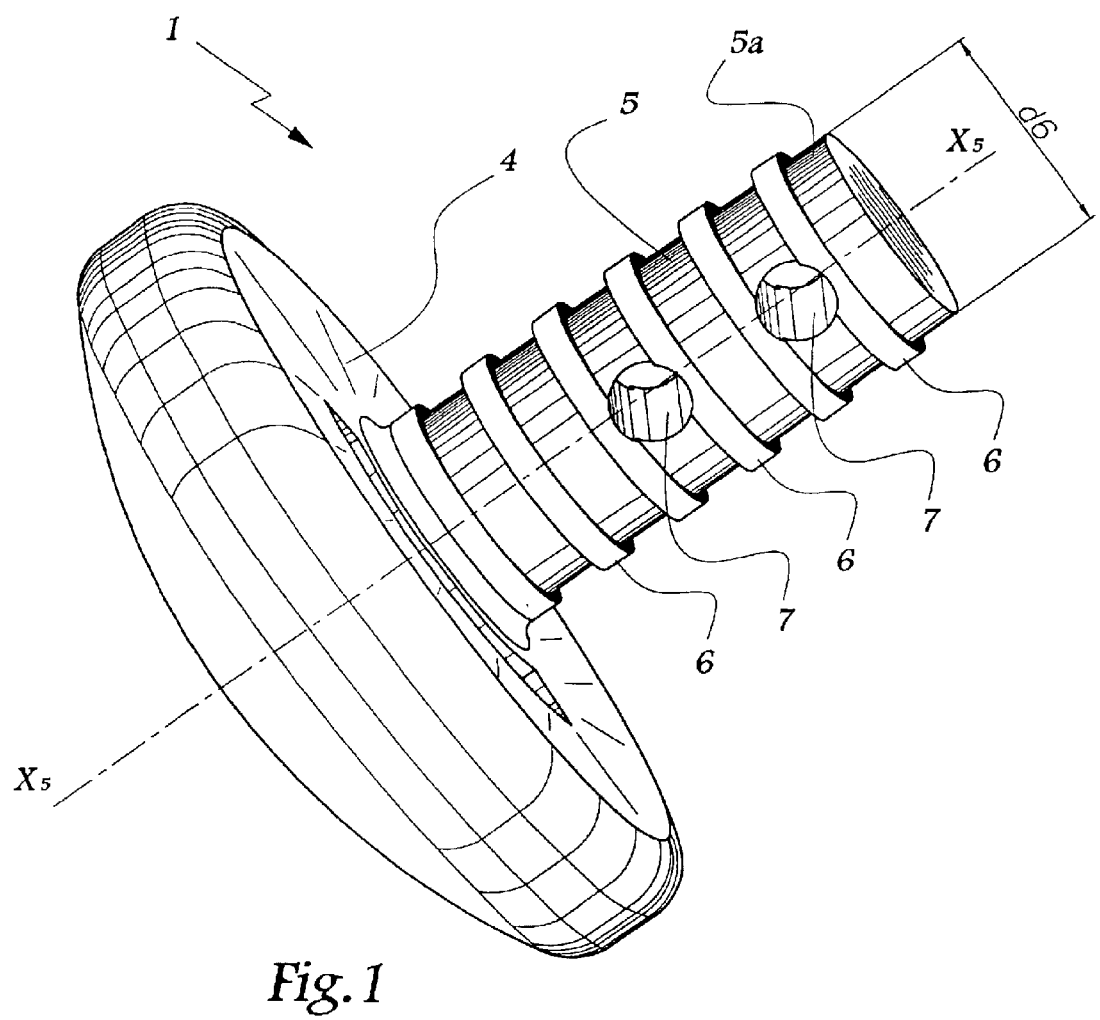
FIG. 1 is a view in perspective of an implant according to the invention.
Figure 2:
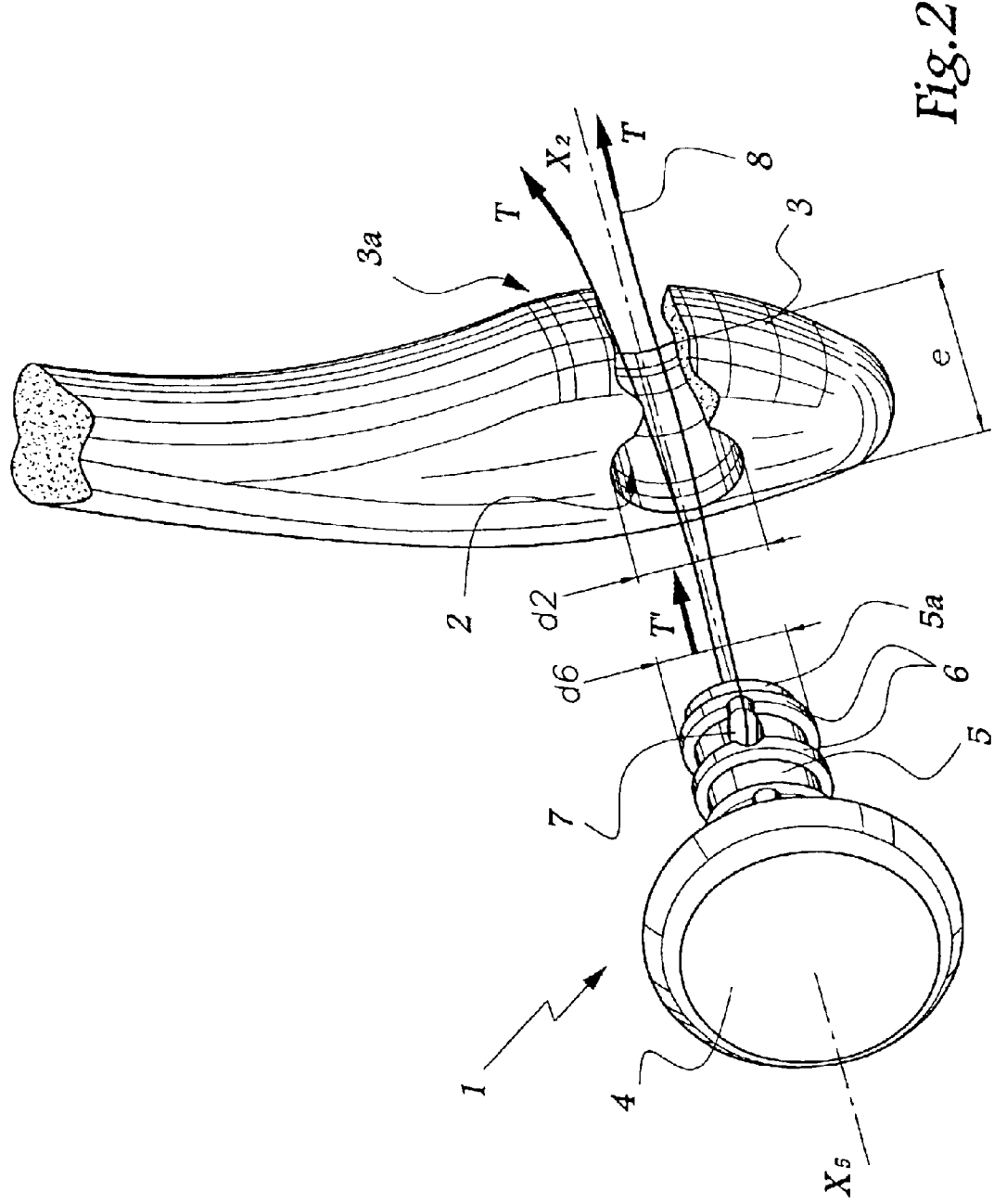
FIG. 2 is a view in perspective of the implant of FIG. 1 during positioning in a fibular malleolus, shown with parts torn away.

Referring now to the drawings, the implant 1 shown in FIGS. 1 and 2 is intended to be introduced in a bore 2 made in the lateral or fibular malleolus 3. The implant 1 comprises a convex head 4, substantially in the form of a spherical cap and of which the radius of curvature is substantially equal to that of the outer cheek of the astragalus of the ankle in question. The shank 5 of the implant 1 is provided with outer radial flanges 6 of which the outer diameter $d_6$ is substantially equal to the inner diameter $d_2$ of the bore 2.

According to the invention, two orifices 7 are provided in the shank 5 and are capable of receiving a suture thread 8 or other flexible tie. When such a thread is engaged in one of the orifices 7, it is possible to exert on the thread 8 an effort of traction T which is transmitted by the thread 8 to the shank 5 as represented by arrow T' in FIG. 2. In this way, by pulling on the thread 8, the surgeon introduces the shank 5 in the bore 2 without having to exert an effort of thrust on the head 4 which may be difficult to access due to the surrounding ligamentary system.

In other words, it suffices for the surgeon to place a thread in one of the orifices 7, to pass the two strands of the thread 8 in the bore 2 via the inner face of the malleolus, then to pull the strands via the outer side of the malleolus. The traction on the thread 8 has the effect of introducing the shank 5 of the implant 1 in the bore 2 and of applying the head 4 on the bone. The effort of traction T exerted on the thread 8 may be intense and directed parallel to the longitudinal axis $X_2$ of the bore 2, with the result that the shank is efficiently drawn towards the inside of the bore 2. In particular, taking into account the direction and intensity of the effort of traction T, the diameters $d_2$ and $d_6$ can be provided to be substantailly equal, with the result that the shank 5 is firmly maintained in place after having been positioned.

The shank 5 is provided with two bores 7 distributed along its axis $X_5$, the bore 7 nearest the end 5*a* of the shank 5 being used. The fact that the shank 5 comprises a plurality of orifices 7 makes it possible to use an orifice 7 relatively close to the end 5*a* of the shank 5 and to avail of such an orifice including when the shank 5 is cut in order to adapt its length to the thickness e of the malleolus 3. The number of bores 7 may, of course, be increased if necessary.

Figure 3:
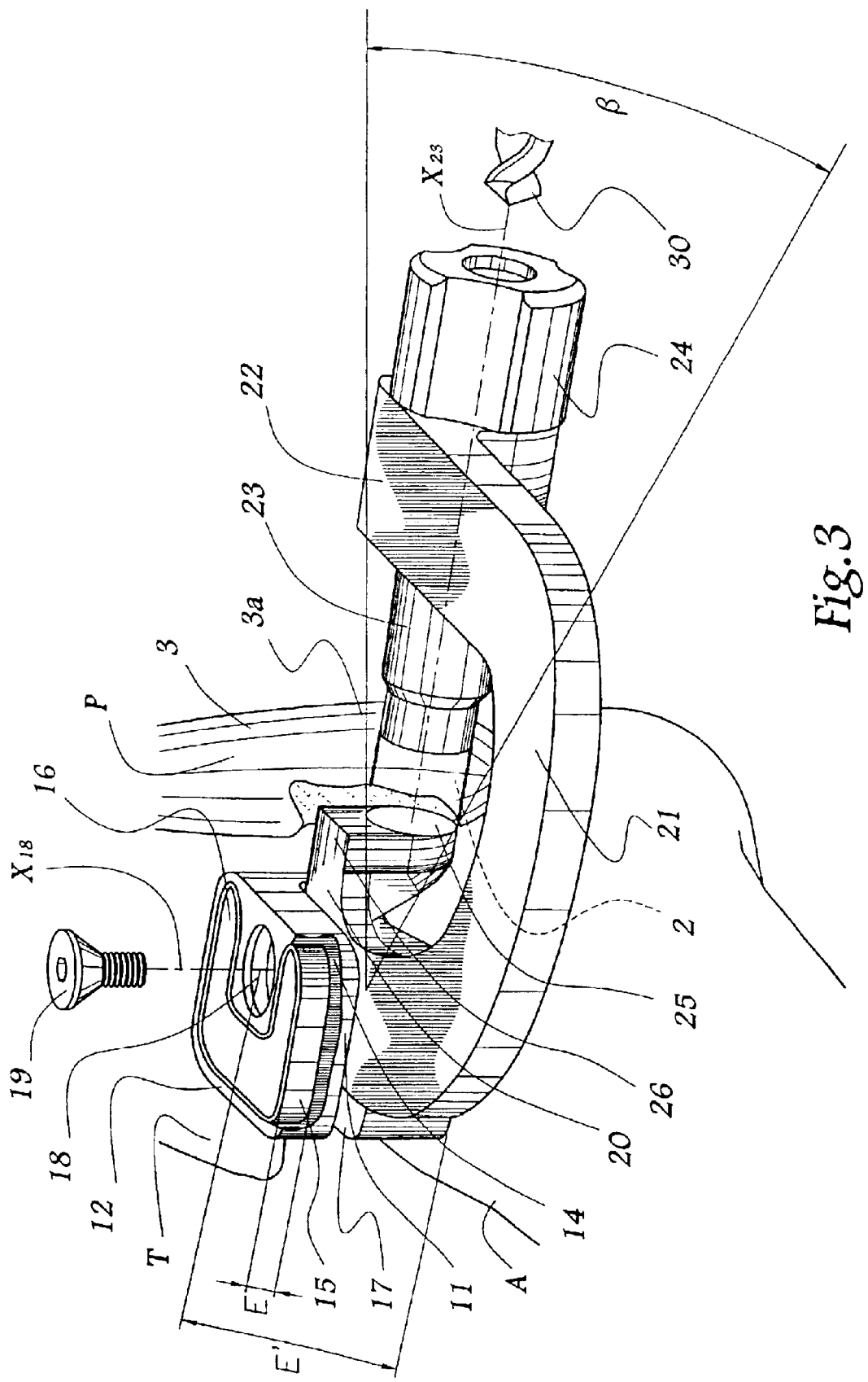
FIG. 3 schematically shows, with parts torn away, an ancillary tool for placing the implant of FIG. 1, in the course of use.
Figure 4:
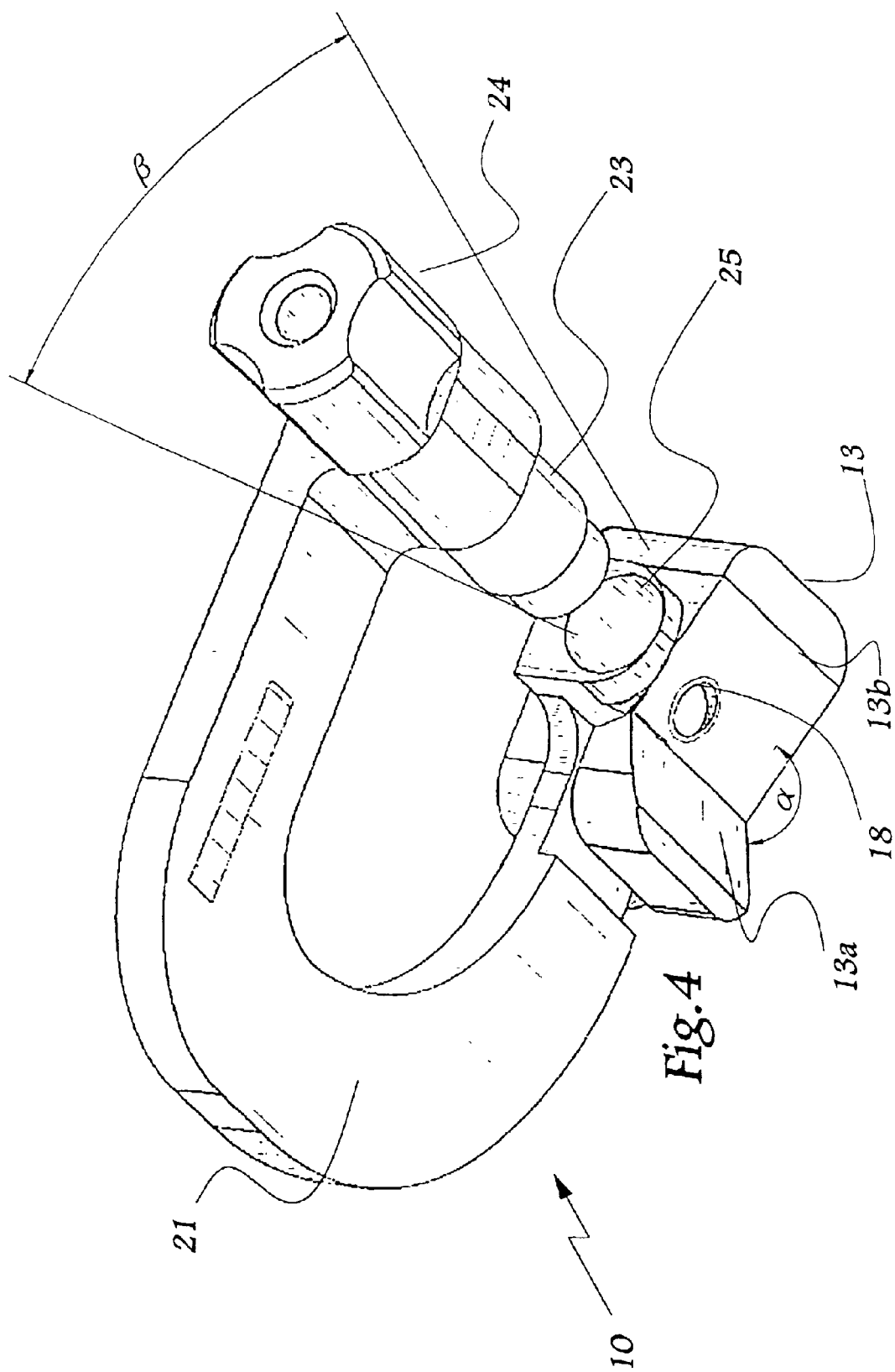
FIG. 4 is a view in perspective of the tool of FIG. 3, from underneath.

The bore 2 is made via the outer face 3*a* of the malleolus 3 with the aid of the ancillary tool shown in FIGS. 3 and 4. This tool 10 comprises a spacer block 11 provided to be disposed between the tibia T and the astragalus A of an ankle to be fitted with the implant 1. The block 11 comprises a substantially planar upper surface 12 intended to cooperate with a planar surface created by resection of the distal end of the tibia T. The lower surface 13 of the block 11 is formed by two planar surfaces 13*a* and 13*b* inclined with respect to each other by an angle α, the surfaces 13*a* and 13*b* being provided to bear respectively on corresponding surfaces created by resection of the upper face of the astragalus A.

The surface 12 of the block 11 comprises a C-shaped housing 14 intended to receive a shim 15 of which the upper surface 16 is in contact with the lower surface of the tibia T. The thickness E of the shim 15 shown in FIG. 3 is such that its upper surface 16 is flush with the upper surface 12 of the block 11.

However, thicker shims may be used when the distance E' between the lower surface of the tibia and upper surface of the astragalus is greater than in the configuration shown in FIG. 3.

The block 11 defines a housing 17 for receiving the end 20 of a substantially C-shaped lug 21. The end 20 is provided with a bore (not shown) which, in the configuration of FIGS. 3 and 4, is aligned with a bore 18 made in the block 11 and passing downwardly through this block, i.e. connecting the surfaces 12 and 13. A screw 19 may be introduced in this bore which is at least partially tapped, this making it possible to immobilize the end 20 of the lug 21 inside the housing 17. In practice, the clearance made when the screw 19 is tightened allows a limited pivoting about axis $X_{18}$ of the bore 18.

At its end 22 opposite the end 20, the lug 21 supports a clamping system 23 adapted to be manoevred thanks to a knurl 24 and making it possible to apply the malleolus 3 of the fibula P against a stop 25 formed on an extension 26 of the end 20 of the lug 21. $X_{23}$ denotes the longitudinal axis of these clamping means. The clamping means 23 are hollow, with the result that a drill 30 may be introduced up to the level of the outer face 3*a* of the malleolus 3 in order to make the bore 2 from the outside towards the inside of the malleolus 3. In this way, the surgeon may easily aim at the suitable part of the malleolus 3 thanks to the clamping means 23 which also constitute a bore guide for the drill 30.

As the lug 21 is capable of pivoting about axis $X_{18}$, the position of axis $X_{23}$ is variable in pivoting about this axis $X_{18}$, which makes it possible optimally to adjust the orientation of the bore 2 as a function of the exact geometry of the malleolus 3. β denotes the maximum angle of pivoting of the axis $X_{23}$ about axis $X_{18}$. In practice, the angle β is of the order of 10°.

Thanks to the tool 10, a bore 2 may therefore be formed from the outside, allowing a rapid and efficient implantation of the implant 1.

When shims 15 of thickness greater than those shown in FIG. 2 are used, they can be provided to overlap the bore 18, as the screw 19 is placed in position before positioning of the shim 15 which is effected during operation as a function of the distance E'.

The invention has been shown with a total ankle prosthesis, which corresponds to the geometry of the surfaces 12 and 13 of the block 11. However, it is also applicable to a partial ankle prosthesis, without modification of the implant 1, the ancillary tool in that case being adapted to the geometry of the anatomical articulation surfaces between the tibia and the astragalus.

What is claimed is:

1. A method of positioning a malleolar implant for partial or total ankle prosthesis wherein a bore in a fibula such that a surface of a head of the implant engages an astragalus or astragalian prosthetic component, the method including:
   a. providing at least one orifice through a shank of the implant so as to extend generally transverse to an elongated axis of the shank;
   b. inserting a flexible traction member through said at least one orifice;
   c. extending the flexible traction member along the shank in a direction away from the head of the implant and through the bore through the fibula;
   d. aligning the shank with the bore through the fibula; and
   e. applying a force on the flexible traction member to pull the shank into the bore and urge the surface of the head against the astragalus or astragalian prosthetic component.

2. The method of claim 1 including providing the shank with a plurality of spaced orifices.

3. The method of claim 1 including providing the shank with a plurality of radially extending flanges for frictionally seating the shank within the bore of the fibula.

* * * * *